US008426802B2

(12) United States Patent
Giles et al.

(10) Patent No.: US 8,426,802 B2
(45) Date of Patent: Apr. 23, 2013

(54) MASS SPECTROMETER

(75) Inventors: Kevin Giles, Cheshire (GB); Steven Derek Pringle, Darwen (GB); Jason Lee Wildgoose, Stockport (GB)

(73) Assignee: Micromass UK Limited, Manchester (GB)

(*) Notice: Subject to any disclaimer, the term of this patent is extended or adjusted under 35 U.S.C. 154(b) by 548 days.

(21) Appl. No.: 12/518,291

(22) PCT Filed: Dec. 12, 2007

(86) PCT No.: PCT/GB2007/004774
§ 371 (c)(1),
(2), (4) Date: Oct. 16, 2009

(87) PCT Pub. No.: WO2008/071967
PCT Pub. Date: Jun. 19, 2008

(65) Prior Publication Data
US 2010/0032561 A1    Feb. 11, 2010

Related U.S. Application Data

(60) Provisional application No. 60/884,498, filed on Jan. 11, 2007.

(30) Foreign Application Priority Data

Dec. 12, 2006  (GB) .................................. 0624740.7

(51) Int. Cl.
*B01D 59/44* (2006.01)
*H01J 49/00* (2006.01)

(52) U.S. Cl.
USPC ........... 250/281; 250/282; 250/283; 250/285; 250/290; 250/292; 250/294; 250/287

(58) Field of Classification Search .......... 250/281–283, 250/285, 290, 292, 294
See application file for complete search history.

(56) References Cited

U.S. PATENT DOCUMENTS 6,111,250 A    8/2000 Thomson et al.
6,630,662 B1 * 10/2003 Loboda ......................... 250/281
6,812,453 B2 * 11/2004 Bateman et al. .............. 250/287

(Continued)

FOREIGN PATENT DOCUMENTS
WO     92/14259     8/1992
WO    2004030129    9/2003

OTHER PUBLICATIONS

Steven Pringle, Kevin Giles, Jason Wildgoose, Jonathan Williams, Susan Slade Konstantinos Thalassinos, Robert Bateman, "An investigation of mobility separation of some peptide and protein ions using a new hybrid quadrupole/travelling wave IMS/oa-TOF instrument", International Journal of Mass Spectrometry 2007, vol. 261, issue 1, pp. 1-12.*

*Primary Examiner* — Nikita Wells
*Assistant Examiner* — Meenakshi Sahu
(74) *Attorney, Agent, or Firm* — Diederiks & Whitelaw, PLC

(57) ABSTRACT

A mass spectrometer is disclosed comprising a device which is operable in a first mode of operation to separate ions temporally according to their ion mobility by applying a continuous axial electric field. The device is also operable in a second mode of operation wherein ions are separated temporally according to the their mass to charge ratio by pulsing an applied axial electric field ON and OFF.

19 Claims, 5 Drawing Sheets

U.S. PATENT DOCUMENTS

| | | | |
|---|---|---|---|
| 7,829,841 B2 * | 11/2010 | Bateman et al. | 250/281 |
| 8,153,960 B2 * | 4/2012 | Giles et al. | 250/282 |
| 8,283,626 B2 * | 10/2012 | Brown et al. | 250/282 |
| 2005/0253064 A1 * | 11/2005 | Loboda et al. | 250/292 |
| 2009/0173880 A1 * | 7/2009 | Bateman et al. | 250/292 |
| 2010/0065737 A1 | 3/2010 | Bateman et al. | |
| 2010/0327157 A1 * | 12/2010 | Green et al. | 250/282 |

* cited by examiner

MASS SPECTROMETER

CROSS REFERENCE TO RELATED APPLICATIONS

This application is the National Stage of International Application No. PCT/GB2007/004774, filed Dec. 12, 2007, which claims priority to and benefit of U.S. Provisional Patent Application Ser. No. 60/884,498, filed Jan. 11, 2007, and United Kingdom Patent Application No. 0624740.7, filed Dec. 12, 2006. The entire contents of these applications are incorporated herein by reference.

BACKGROUND OF THE INVENTION

The present invention relates to a mass spectrometer and a method of mass spectrometry.

Ion mobility spectrometry ("IMS") is a well established analytical technique where ionic species are separated according to their ion mobility by subjecting the ions to a weak electric field in the presence of a buffer gas. A known ion mobility spectrometer comprises a linear tube filled with gas. A static homogeneous electric field is maintained along the length of the tube. Ions experience a force in one direction due to the electric field and an effective force in the opposite direction due to collisions with the buffer gas. To a first approximation, the equation of motion of an ion within the known ion mobility spectrometer can be written as:

$$\frac{d^2}{dt^2}x + \frac{\lambda}{m}\left(\frac{d}{dt}x\right) = E\frac{q}{m} \quad (1)$$

wherein t is time, x is the axial position along the length of the ion mobility spectrometer, $\lambda$ is the drag coefficient, m is the mass of the ion, E is the electric field strength and q is the charge on the ion.

In this regime ions quickly reach a steady state velocity and the average acceleration becomes zero. Under these conditions the above equation of motion reduces to:

$$\frac{d}{dt}x = E\frac{q}{\lambda} \quad (2)$$

In Eqn. 2, the ratio q/$\lambda$ is termed the ion mobility K. Ions having a relatively low ion mobility reach a lower steady state velocity than ions having a relatively high ion mobility and thus take longer to traverse the length of the ion mobility spectrometer.

Another known ion mobility spectrometer comprises a series of ring electrodes. A two-phase RF voltage is applied to the ring electrodes in order to create a radial pseudo-potential well which acts to confine ions radially within the ion mobility spectrometer. A series of pulses or transient DC voltages are applied to the electrodes and are translated along the length of the ion mobility spectrometer. The ability of an ion to keep up with the series of DC pulses which are translated along the length of the ion mobility spectrometer is a function of the mobility of the ion. Relatively low mobility ions are overtaken by the transient DC voltage more often than ions having a relatively high mobility. As a result, ions having a relatively high ion mobility are preferentially urged along the length of the ion mobility spectrometer whereas ions having a relatively low ion mobility take a relatively long time to traverse the length of the ion mobility spectrometer.

It is known to couple an ion mobility spectrometer to either a quadrupole rod set mass analyser or an orthogonal acceleration Time of Flight mass analyser. The separating characteristics of the known ion mobility spectrometer enable the duty cycle and sensitivity of either the quadrupole rod set mass analyser or the Time of Flight mass analyser to be improved. Furthermore, determining the drift time of ions through the known ion mobility spectrometer also reveals structural information about the ions.

It is desired to provide an improved mass spectrometer.

SUMMARY OF THE INVENTION

According to an aspect of the present invention there is provided a mass spectrometer comprising:

a device for separating ions temporally, wherein in a first mode of operation the device is arranged and adapted to separate ions temporally according to their ion mobility and wherein in a second mode of operation the device is arranged and adapted to separate ions according to their mass to charge ratio.

The device preferably comprises an ion guide comprising a plurality of electrodes.

The ion guide preferably comprises: (i) a multipole rod set or a segmented multipole rod set; (ii) an ion tunnel or ion funnel; or (iii) a stack or array of planar, plate or mesh electrodes.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area.

According to the preferred embodiment at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) ≦1.0 mm; (ii) ≦2.0 mm; (iii) ≦3.0 mm; (iv) ≦4.0 mm; (v) ≦5.0 mm; (vi) ≦6.0 mm; (vii) ≦7.0 mm; (viii) ≦8.0 mm; (ix) ≦9.0 mm; (x) ≦10.0 mm; and (xi) >10.0 mm. The stack or array of planar, plate or mesh electrodes comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use. Preferably, at least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are supplied with an AC or RF voltage and wherein adjacent planar, plate or mesh electrodes are supplied with opposite phases of the AC or RF voltage.

The ion guide preferably comprises a plurality of axial segments or at least 5, 10, 15, 20, 25, 30, 35, 40, 45, 50, 55, 60, 65, 70, 75, 80, 85, 90, 95 or 100 axial segments.

The centre to centre spacing between adjacent electrodes is preferably selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) 5.0-5.5 mm; (xii) 5.5-6.0 mm; (xiii) 6.0-6.5 mm; (xiv) 6.5-7.0 mm; (xv) 7.0-7.5 mm; (xvi) 7.5-8.0 mm; (xvii) 8.0-8.5 mm; (xviii) 8.5-9.0 mm; (xix) 9.0-9.5 mm; (xx) 9.5-10.0 mm; and (xxi) >10.0 mm.

The ion guide preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The mass spectrometer preferably further comprises first means arranged and adapted to confine ions radially within the device. The first means preferably comprises first AC or RF voltage means arranged and adapted to apply a first AC or RF voltage to at least 5%, 10%, 15%, 20%, 25%, 30%, 35%, 40%, 45%, 50%, 55%, 60%, 65%, 70%, 75%, 80%, 85%, 90%, 95% or 100% of the electrodes forming the ion guide in order to confine ions radially within the ion guide.

The first AC or RF voltage means is preferably arranged and adapted to supply a first AC or RF voltage to the electrodes of the ion guide having an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The first AC or RF voltage means is preferably arranged and adapted to supply a first AC or RF voltage to the electrodes of the ion guide having a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The phase difference of the first AC or RF voltage between adjacent electrodes or adjacent groups of electrodes is preferably selected from the group consisting of: (i) >0°; (ii) 1-30°; (iii) 30-60°; (iv) 60-90°; (v) 90-120°; (vi) 120-150°; (vii) 150-180°; (viii) 180 20; (ix) 180-210°; (x) 210-240°; (xi) 240-270°; (xii) 270-300°; (xiii) 300-330°; and (xiv) 330-360°.

The first AC or RF voltage is preferably applied, in use, to the electrodes and preferably causes or generates a radial pseudo-potential well which acts to confine ions radially, in use, within the ion guide.

The first AC or RF voltage preferably comprises a two-phase or multi-phase AC or RF voltage.

According to the preferred embodiment the mass spectrometer preferably further comprises a second means which is arranged and adapted to apply an axial electric field along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

In the first mode of operation the second means is preferably arranged and adapted to apply the axial electric field substantially continuously.

In the first mode of operation the maximum amplitude of the axial electric field at one or more points along the axial length of the device may be arranged to remain substantially constant with time. In the first mode of operation the maximum amplitude of the axial electric field at one or more points along the axial length of the device may alternatively be arranged to vary, increase or decrease with time or wherein the maximum amplitude may be arranged to be ramped, stepped, scanned or varied linearly or non-linearly with time.

The second means preferably further comprises a DC voltage means for maintaining in the first mode of operation a non-zero DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The mass spectrometer preferably further comprises means arranged and adapted to vary, increase, or decrease the DC voltage gradient with time or to ramp, step, scan or linearly or non-linearly vary the DC voltage gradient with time.

The second means preferably further comprises means for applying one or more DC voltages to at least some of the electrodes forming the device wherein the amplitude of the DC voltage is arranged to vary, increase or decrease with time or wherein the DC voltage is ramped, stepped, scanned or varied linearly or non-linearly with time in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second means preferably further comprises means for applying a single phase AC or RF voltage to at least some of the electrodes forming the device wherein all electrodes are maintained at substantially the same phase and wherein an axial pseudo-potential is generated which acts to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second means is preferably further arranged to vary, increase or decrease the amplitude of the axial pseudo-potential with time or wherein the axial pseudo-potential is ramped, stepped, scanned or varied linearly or non-linearly with time.

The second means preferably further comprises transient DC voltage means arranged and adapted in the first mode of operation to apply one or more transient DC voltages or potentials or one or more transient DC voltage or potential waveforms to at least some of the electrodes forming the device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second means is preferably further arranged to vary, increase or decrease the amplitude of the one or more transient DC voltages or potentials or the one or more transient DC voltage or potential waveforms with time or wherein the amplitude of the one or more transient DC voltages or potentials or the one or more transient DC voltage or potential waveforms is ramped, stepped, scanned or varied linearly or non-linearly with time.

In the first mode of operation the one or more transient DC voltages or potentials or the one or more transient DC voltage or potential waveforms are preferably translated along the axial length of the device at a velocity selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii)

1700-1800 m/s; (xix) 1800-1900 m/s; (xx) 1900-2000 m/s; (xxi) 2000-2100 m/s; (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi) >3000 m/s.

According to an embodiment the velocity or speed at which the one or more transient DC voltage or potentials or the one or more transient DC voltage or potential waveforms are translated along or applied to the electrodes forming the device may be varied as a function of time. According to an embodiment the velocity of speed at which the one or more transient DC voltages or potentials are translated or applied to the electrodes may be varied, increased or decreased with time. According to one embodiment the velocity or speed of the one or more transient DC voltages or potentials may be ramped, stepped, scanned or varied linearly or non-linearly with time. An embodiment is contemplated wherein, for example, the preferred ion mobility-mass analyser may change from an ion mobility separation mode of operation to a mass to charge ratio separation mode of operation (or vice versa) as the speed of the travelling wave or the one or more transient DC voltage or potentials is increased, decreased or varied.

The mass spectrometer may further comprise AC or RF voltage means arranged and adapted in the first mode of operation to apply two or more phase-shifted AC or RF voltages to electrodes forming the device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

In the first mode of operation ions are preferably accelerated within the device so that they substantially achieve a terminal velocity.

In the first mode of operation singly charged ions having a mass to charge ratio in the range of 1-100, 100-200, 200-300, 300-400, 400-500, 500-600, 600-700, 700-800, 800-900, 900-1000 or >1000 preferably have a drift or transit time through the device in the range: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) 70-75 ms; (xl) 75-80 ms; (xli) 80-85 ms; (xlii) 85-90 ms; (xliii) 90-95 ms; (xliv) 95-100 ms; and (xlv) >100 ms.

In the first mode of operation the scan or cycle time of the device is preferably selected from the group consisting of: (i) 0-1 ms; (ii) 1-2 ms; (iii) 2-3 ms; (iv) 3-4 ms; (v) 4-5 ms; (vi) 5-6 ms; (vii) 6-7 ms; (viii) 7-8 ms; (ix) 8-9 ms; (x) 9-10 ms; (xi) 10-11 ms; (xii) 11-12 ms; (xiii) 12-13 ms; (xiv) 13-14 ms; (xv) 14-15 ms; (xvi) 15-16 ms; (xvii) 16-17 ms; (xviii) 17-18 ms; (xix) 18-19 ms; (xx) 19-20 ms; (xxi) 20-21 ms; (xxii) 21-22 ms; (xxiii) 22-23 ms; (xxiv) 23-24 ms; (xxv) 24-25 ms; (xxvi) 25-26 ms; (xxvii) 26-27 ms; (xxviii) 27-28 ms; (xxix) 28-29 ms; (xxx) 29-30 ms; (xxxi) 30-35 ms; (xxxii) 35-40 ms; (xxxiii) 40-45 ms; (xxxiv) 45-50 ms; (xxxv) 50-55 ms; (xxxvi) 55-60 ms; (xxxvii) 60-65 ms; (xxxviii) 65-70 ms; (xxxix) $70-75$ ms; (xl) 75-80 ms; (xli) 80-85 ms; (xlii) 85-90 ms; (xliii) 90-95 ms; (xliv) 95-100 ms; and (xlv) >100 ms.

In the first mode of operation at least a portion of the device is preferably arranged to be maintained at a pressure selected from the group consisting of: (i) >0.001 mbar; (ii) >0.01 mbar; (iii) >0.1 mbar; (iv) >1 mbar; (v) >10 mbar; (vi) >100 mbar; (vii) >1000 mbar; (viii) 0.001-1000 mbar; (ix) 0.001-0.1 mbar; (x) 0.1-10 mbar; and (xi) 10-1000 mbar.

In the first mode of operation at least a portion of the device is preferably arranged to be maintained at a pressure selected from the group consisting of: ((i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

According to a preferred embodiment the device may be operated at relatively high pressures including sub-atmospheric pressures. According to an embodiment the device may be operated at atmospheric pressure in the first mode of operation.

In the second mode of operation the second means is preferably arranged and adapted to apply an axial electric field in a pulsed or time varying manner.

In the second mode of operation the second means is preferably arranged in one cycle to apply or maintain the axial electric field at a first amplitude A1 for a first time period t1 and to apply or maintain the axial electric field at a second amplitude A2 for a second time period t2. The ratio A1/A2 is preferably selected from the group consisting of: (i) <−1000; (ii) −1000 to −500; (iii) −500 to −100; (iv) −100 to −50; (v) −50 to −10; (vi) −10 to −5; (vii) −5 to 0; (viii) 0-5; (ix) 5-10; (x) 10-50; (xi) 50-100; (xii) 100-500; (xiii) 500-1000; and (xiv) $\geq$1000.

According to an embodiment the axial electric field may be switched ON for a first time period t1 and may then be switched OFF or reduced in amplitude or intensity for a second time period t2. However, other embodiments are contemplated wherein the axial electric field may be applied in the reverse direction during the second time period t2. According to this embodiment an axial electric field having a first amplitude A1 may be applied in a first direction for a first time period t1 and then an axial electric field having a second amplitude A2 may be applied in a second direction (which is preferably orthogonal to or opposed to the first direction) for a second time period t2. This embodiment enables the resolution or separation characteristics of the preferred ion mobility-mass analyser to be improved or enhanced.

According to the preferred embodiment A2 is preferably zero.

The ratio t1/t2 is preferably selected from the group consisting of: (i) <0.01; (ii) 0.01-0.02; (iii) 0.02-0.03; (iv) 0.03-0.04; (v) 0.04-0.05; (vi) 0.05-0.06; (vii) 0.06-0.07; (viii) 0.07-0.08; (ix) 0.08-0.09; (x) 0.09-0.10; (xi) 0.10-0.11; (xii) 0.11-0.12; (xiii) 0.12-0.13; (xiv) 0.13-0.14; (xv) 0.14-0.15; (xvi) 0.15-0.16; (xvii) 0.16-0.17; (xviii) 0.17-0.18; (xix) 0.18-0.19; (xx) 0.19-0.20; (xxi) 0.20-0.21; (xii) 0.21-0.22; (xxiii) 0.22-0.23; (xxiv) 0.23-0.24; (xxv) 0.24-0.25; (xxvi) 0.25-0.26; (xxvii) 0.26-0.27; (xxviii) 0.27-0.28; (xxix) 0.28-0.29; (xxx) 0.29-0.30; (xxxi) 0.30-0.31; (xxxii) 0.31-0.32; (xxxiii) 0.32-0.33; (xxxiv) 0.33-0.34; (xxxv) 0.34-0.35; (xxxvi) 0.35-0.36; (xxxvii) 0.36-0.37; (xxxviii) 0.37-0.38; (xxxix) 0.38-0.39; (xl) 0.39-0.40; (xli) 0.40-0.41; (xlii) 0.41-0.42; (xliii) 0.42-0.43; (xliv) 0.43-0.44; (xlv) 0.44-0.45; (xlvi) 0.45-0.46; (xlvii) 0.46-0.47; (xlviii) 0.47-0.48; (xlix) 0.48-0.49; and (1) 0.49-0.50.

The ratio t1/t2 is preferably selected from the group consisting of: (i) 0.50-0.51; (ii) 0.51-0.52; (iii) 0.52-0.53; (iv) 0.53-0.54; (v) 0.54-0.55; (vi) 0.55-0.56; (vii) 0.56-0.57; (viii) 0.57-0.58; (ix) 0.58-0.59; (x) 0.59-0.60; (xi) 0.60-0.61; (xii) 0.61-0.62; (xiii) 0.62-0.63; (xiv) 0.63-0.64; (xv) 0.64-0.65; (xvi) 0.65-0.66; (xvii) 0.66-0.67; (xviii) 0.67-0.68; (xix)

0.68-0.69; (xx) 0.69-0.70; (xxi) 0.70-0.71; (xii) 0.71-0.72; (xxiii) 0.72-0.73; (xxiv) 0.73-0.74; (xxv) 0.74-0.75; (xxvi) 0.75-0.76; (xxvii) 0.76-0.77; (xxviii) 0.77-0.78; (xxix) 0.78-0.79; (xxx) 0.79-0.80; (xxxi) 0.80-0.81; (xxxii) 0.81-0.82; (xxxiii) 0.82-0.83; (xxxiv) 0.83-0.84; (xxxv) 0.84-0.85; (xxxvi) 0.85-0.86; (xxxvii) 0.86-0.87; (xxxviii) 0.87-0.88; (xxxix) 0.88-0.89; (xl) 0.89-0.90; (xli) 0.90-0.91; (xlii) 0.91-0.92; (xliii) 0.92-0.93; (xliv) 0.93-0.94; (xlv) 0.94-0.95; (xlvi) 0.95-0.96; (xlvii) 0.96-0.97; (xlviii) 0.97-0.98; (xlix) 0.98-0.99; and (l) 0.99-1.00.

The ratio t1/t2 is preferably selected from the group consisting of: (i) 1.0-1.5; (ii) 1.5-2.0; (iii) 2.0-2.5; (iv) 2.5-3.0; (v) 3.0-3.5; (vi) 3.5-4.0; (vii) 4.0-4.5; (viii) 4.5-5.0; (ix) 5.0-5.5; (x) 5.5-6.0; (xi) 6.0-6.5; (xii) 6.5-7.0; (xiii) 7.0-7.5; (xiv) 7.5-8.0; (xv) 8.0-8.5; (xvi) 8.5-9.0; (xvii) 9.0-9.5; (xviii) 9.5-10.0; and (xix) >10.

In the second mode of operation the maximum amplitude of the axial electric field at one or more points along the axial length of the device may be arranged to remain substantially constant with time.

In the second mode of operation the maximum amplitude of the axial electric field at one or more points along the axial length of the device may be arranged to vary, increase, or decrease with time or wherein the maximum amplitude may be arranged to be ramped, stepped, scanned or varied linearly or non-linearly with time.

The second means preferably further comprises a DC voltage means for maintaining in the second mode of operation a non-zero DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The mass spectrometer preferably further comprises means arranged and adapted to vary, increase or decrease the DC voltage gradient with time or to ramp, step, scan or linearly or non-linearly vary the DC voltage gradient with time.

According to an embodiment the second means further comprises means for applying one or more DC voltages to at least some of the electrodes forming the device wherein the amplitude of the DC voltage is arranged to vary, increase or decrease with time or wherein the DC voltage is ramped, stepped, scanned or varied linearly or non-linearly with time in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second means preferably further comprises means for applying a single phase AC or RF voltage to at least some of the electrodes forming the device wherein all electrodes are maintained at substantially the same phase and wherein an axial pseudo-potential is generated which acts to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device. The axial pseudo-potential is preferably translated along at least a portion of the axial length of the device.

The second means is preferably further arranged to vary, increase or decrease the amplitude of the pseudo-potential with time or wherein the axial pseudo-potential is ramped, stepped, scanned or varied linearly or non-linearly with time.

According to an embodiment the second means may comprise means for applying a time varying, AC, RF or sinusoidal like or shaped profile axial DC electric field or an inhomogeneous DC axial electric field to at least some of the electrodes forming the device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

The second means preferably further comprises transient DC voltage means arranged and adapted in the second mode of operation to apply one or more transient DC voltages or potentials or one or more transient DC voltage or potential waveforms to at least some of the electrodes forming the device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

According to an embodiment the second means is further arranged to vary, increase or decrease the amplitude of the one or more transient DC voltages or potentials or the one or more transient DC voltage or potential waveforms with time or wherein the amplitude of the one or more transient DC voltages or potentials or the one or more transient DC voltage or potential waveforms is preferably ramped, stepped, scanned or varied linearly or non-linearly with time.

In the second mode of operation the one or more transient DC voltages or potentials or the one or more transient DC voltage or potential waveforms are preferably translated along the axial length of the device at a velocity selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii) 1700-1800 m/s; (xix) 1800-1900 m/s; (xx) 1900-2000 m/s; (xxi) 2000-2100 m/s; (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi) >3000 m/s.

The mass spectrometer preferably further comprises AC or RF voltage means arranged and adapted in the second mode of operation to apply two or more phase-shifted AC or RF voltages to electrodes forming the device in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the device.

In the second mode of operation ions are preferably accelerated within the device but are substantially prevented from achieving a terminal velocity or wherein the ions do not achieve a terminal velocity.

In the second mode of operation singly charged ions having a mass to charge ratio in the range of 1-100, 100-200, 200-300, 300-400, 400-500, 500-600, 600-700, 700-800, 800-900, 900-1000 or >1000 preferably have a drift or transit time through the device in the range: (i) 0-5 ms; (ii) 5-10 ms; (iii) 10-15 ms; (iv) 15-20 ms; (v) 20-25 ms; (vi) 25-30 ms; (vii) 30-35 ms; (viii) 35-40 ms; (ix) 40-45 ms; (x) 45-50 ms; (xi) 50-55 ms; (xii) 55-60 ms; (xiii) 60-65 ms; (xiv) 65-70 ms; (xv) 70-75 ms; (xvi) 75-80 ms; (xvii) 80-85 ms; (xviii) 85-90 ms; (xix) 90-95 ms; (xx) 95-100 ms; (xxi) 100-110 ms; (xxii) 110-120 ms; (xxiii) 120-130 ms; (xxiv) 130-140 ms; (xxv) 140-150 ms; (xxvi) 150-160 ms; (xxvii) 160-170 ms; (xxviii) 170-180 ms; (xxix) 180-190 ms; (xxx) 190-200 ms; (xxxi) 200-250 ms; (xxxii) 250-300 ms; (xxxiii) 300-350 ms; (xxxiv) 350-400 ms; (xxxv) 400-450 ms; (xxxvi) 450-500 ms; and (xxxvii) >500 ms.

In the second mode of operation the scan or cycle time of the device is preferably selected from the group consisting of: (i) 0-5 ms; (ii) 5-10 ms; (iii) 10-15 ms; (iv) 15-20 ms; (v) 20-25 ms; (vi) 25-30 ms; (vii) 30-35 ms; (viii) 35-40 ms; (ix) 40-45 ms; (x) 45-50 ms; (xi) 50-55 ms; (xii) 55-60 ms; (xiii) 60-65 ms; (xiv) 65-70 ms; (xv) 70-75 ms; (xvi) 75-80 ms; (xvii) 80-85 ms; (xviii) 85-90 ms; (xix) 90-95 ms; (xx) 95-100 ms; (xxi) 100-110 ms; (xxii) 110-120 ms; (xxiii) 120-130 ms; (xxiv) 130-140 ms; (xxv) 140-150 ms; (xxvi) 150-160 ms; (xxvii) 160-170 ms; (xxviii) 170-180 ms; (xxix) 180-190 ms; (xxx) 190-200 ms; (xxxi) 200-250 ms; (xxxii) 250-300 ms; (xxxiii) 300-350 ms; (xxxiv) 350-400 ms; (xxxv) 400-450 ms; (xxxvi) 450-500 ms; and (xxxvii) >500 ms.

In the second mode of operation at least a portion of the device is preferably arranged to be maintained at a pressure selected from the group consisting of: (i) >0.001 mbar; (ii) >0.01 mbar; (iii) >0.1 mbar; (iv) >1 mbar; (v) >10 mbar; (vi) >100 mbar; (vii) >1000 mbar; (viii) 0.001-1000 mbar; (ix) 0.001-0.1 mbar; (x) 0.1-10 mbar; and (xi) 10-1000 mbar.

In the second mode of operation at least a portion of the device is preferably arranged to be maintained at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

According to a preferred embodiment the device may be operated at relatively high pressures including sub-atmospheric pressures. According to an embodiment the device may be operated at atmospheric pressure in the second mode of operation.

In the first mode of operation ions are substantially separated according to their ion mobility.

In the second mode of operation ions are substantially separated according to their mass to charge ratio.

The mass spectrometer preferably further comprises an further ion guide, ion trap or ion trapping region arranged upstream and/or downstream of the device. The further ion guide, ion trap or ion trapping region is preferably arranged to trap, store or accumulate ions and then to periodically pulse ions into or towards the device.

In the first mode of operation and/or the second mode of operation an axial electric field strength at one or more points along the axial length of the device may be arranged to vary, increase or decrease with time or may be arranged to be ramped, stepped, scanned or varied linearly or non-linearly with time in a substantially synchronised manner with the release of ions from the further ion guide, ion trap or ion trapping region arranged upstream and/or downstream of the device.

The device preferably comprises a plurality of electrodes and wherein in the first mode of operation and/or the second mode of operation one or more transient DC voltages or potentials or one or more transient DC voltage or potential waveforms are preferably applied to the electrodes. The amplitude of the one or more transient DC voltages or potentials or the one or more transient DC voltage or potential waveforms is preferably arranged to vary, increase or decrease with time or the amplitude of the one or more transient DC voltages or potentials or the one or more transient DC voltage or potential waveforms is preferably ramped, stepped, scanned or varied linearly or non-linearly with time.

The amplitude of the one or more transient DC voltages or potentials or one or more transient DC voltage or potential waveforms is preferably arranged to vary, increase or decrease with time or the amplitude of the one or more transient DC voltages or potentials or the one or more transient DC voltage or potential waveforms is preferably ramped, stepped, scanned or varied linearly or non-linearly with time in a substantially synchronised manner with the release of ions from an ion guide, ion trap or ion trapping region arranged upstream and/or downstream of the device.

The mass spectrometer preferably further comprises a further mass filter or mass analyser arranged upstream and/or downstream of the device. The further mass filter or mass analyser is preferably selected from the group consisting of: (i) a quadrupole rod set mass filter; (ii) a Time of Flight mass filter or mass analyser;-(iii) a Wein filter; and (iv) a magnetic sector mass filter or mass analyser.

According to an embodiment the mass spectrometer may further comprise a mass analyser arranged upstream and/or downstream of the device. The mass analyser is preferably selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; (xiv) an axial acceleration Time of Flight mass analyser; and (xv) a Wein filter.

One or more mass to charge ratio transmission windows of the mass analyser may be varied, increased or decreased in use or the one or more mass to charge ratio transmission windows may be ramped, stepped, scanned or varied linearly or non-linearly with time. The one or more mass to charge ratio transmission windows of the mass analyser may be preferably varied, increased or decreased in use or one or more mass to charge ratio transmission windows may be ramped, stepped, scanned or varied linearly or non-linearly with time in a substantially synchronised manner with the emergence of ions from the device.

The mass spectrometer preferably further comprises a second ion guide comprising a plurality of electrodes arranged upstream and/or downstream of the device. The second ion guide preferably comprises: (i) a multipole rod set or a segmented multipole rod set; (ii) an ion tunnel or ion funnel; or (iii) a stack or array of planar, plate or mesh electrodes.

The multipole rod set preferably comprises a quadrupole rod set, a hexapole rod set, an octapole rod set or a rod set comprising more than eight rods.

The ion tunnel or ion funnel preferably comprises a plurality of electrodes or at least 2, 5, 10, 20, 30, 40, 50, 60, 70, 80, 90 or 100 electrodes having apertures through which ions are transmitted in use, wherein at least 5%, 10%, 15%, 20%, 25%, 30%, 35%, 40%, 45%, 50%, 55%, 60%, 65%, 70%, 75%, 80%, 85%, 90%, 95% or 100% of the electrodes have apertures which are of substantially the same size or area or which have apertures which become progressively larger and/or smaller in size or in area. Preferably, at least 5%, 10%, 15%, 20%, 25%, 30%, 35%, 40%, 45%, 50%, 55%, 60%, 65%, 70%, 75%, 80%, 85%, 90%, 95% or 100% of the electrodes have internal diameters or dimensions selected from the group consisting of: (i) $\leq 1.0$ mm; (ii) $\leq 2.0$ mm; (iii) $\leq 3.0$ mm; (iv) $\leq 4.0$ mm; (v) $\leq 5.0$ mm; (vi) $\leq 6.0$ mm; (vii) $\leq 7.0$ mm; (viii) $\leq 8.0$ mm; (ix) $\leq 9.0$ mm; (x) $\leq 10.0$ mm; and (xi) >10.0 mm.

The stack or array of planar, plate or mesh electrodes preferably comprises a plurality or at least 2, 3, 4, 5, 6, 7, 8, 9, 10, 11, 12, 13, 14, 15, 16, 17, 18, 19 or 20 planar, plate or mesh electrodes wherein at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are arranged generally in the plane in which ions travel in use.

At least some or at least 5%, 10%, 15%, 20%, 25%, 30%, 35%, 40%, 45%, 50%, 55%, 60%, 65%, 70%, 75%, 80%, 85%, 90%, 95% or 100% of the planar, plate or mesh electrodes are preferably supplied with an AC or RF voltage and wherein adjacent planar, plate or mesh electrodes are supplied with opposite phases of the AC or RF voltage.

The second ion guide preferably comprises a plurality of axial segments or at least 5, 10, 15, 20, 25, 30, 35, 40, 45, 50, 55, 60, 65, 70, 75, 80, 85, 90, 95 or 100 axial segments.

The centre to centre spacing between adjacent electrodes of the second ion guide is preferably selected from the group consisting of: (i) <0.5 mm; (ii) 0.5-1.0 mm; (iii) 1.0-1.5 mm; (iv) 1.5-2.0 mm; (v) 2.0-2.5 mm; (vi) 2.5-3.0 mm; (vii) 3.0-3.5 mm; (viii) 3.5-4.0 mm; (ix) 4.0-4.5 mm; (x) 4.5-5.0 mm; (xi) 5.0-5.5 mm; (xii) 5.5-6.0 mm; (xiii) 6.0-6.5 mm; (xiv) 6.5-7.0 mm; (xv) 7.0-7.5 mm; (xvi) 7.5-8.0 mm; (xvii) 8.0-8.5 mm; (xviii) 8.5-9.0 mm; (xix) 9.0-9.5 mm; (xx) 9.5-10.0 mm; and (xxi) >10.0 mm.

The second ion guide preferably has an axial length selected from the group consisting of: (i) <20 mm; (ii) 20-40 mm; (iii) 40-60 mm; (iv) 60-80 mm; (v) 80-100 mm; (vi) 100-120 mm; (vii) 120-140 mm; (viii) 140-160 mm; (ix) 160-180 mm; (x) 180-200 mm; (xi) 200-220 mm; (xii) 220-240 mm; (xiii) 240-260 mm; (xiv) 260-280 mm; (xv) 280-300 mm; and (xvi) >300 mm.

The mass spectrometer preferably further comprises DC voltage means for maintaining a substantially constant DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide.

The mass spectrometer preferably further comprises transient DC voltage means arranged and adapted to apply one or more transient DC voltages or potentials or one or more transient DC voltage or potential waveforms to at least some of the electrodes forming the second ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide.

The mass spectrometer preferably further comprises AC or RF voltage means arranged and adapted to apply two or more phase-shifted AC or RF voltages to electrodes forming the second ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of the second ion guide.

The mass spectrometer preferably further comprises a collision, fragmentation or reaction device. The collision, fragmentation or reaction device may be provided upstream and/or downstream of the device. The collision, fragmentation or reaction device is preferably arranged and adapted to fragment ions by Collision Induced Dissociation ("CID"). The collision, fragmentation or reaction device may alternatively be selected from the group consisting of: (i) a Surface Induced Dissociation ("SID") fragmentation device; (ii) an Electron Transfer Dissociation fragmentation device; (iii) an Electron Capture Dissociation fragmentation device; (iv) an Electron Collision or Impact Dissociation fragmentation device; (v) a Photo Induced Dissociation ("PID") fragmentation device; (vi) a Laser Induced Dissociation fragmentation device; (vii) an infrared radiation induced dissociation device; (viii) an ultraviolet radiation induced dissociation device; (ix) a nozzle-skimmer interface fragmentation device; (x) an in-source fragmentation device; (xi) an ion-source Collision Induced Dissociation fragmentation device; (xii) a thermal or temperature source fragmentation device; (xiii) an electric field induced fragmentation device; (xiv) a magnetic field induced fragmentation device; (xv) an enzyme digestion or enzyme degradation fragmentation device; (xvi) an ion-ion reaction fragmentation device; (xvii) an ion-molecule reaction fragmentation device; (xviii) an ion-atom reaction fragmentation device; (xix) an ion-metastable ion reaction fragmentation device; (xx) an ion-metastable molecule reaction fragmentation device; (xxi) an ion-metastable atom reaction fragmentation device; (xxii) an ion-ion reaction device for reacting ions to form adduct or product ions; (xxiii) an ion-molecule reaction device for reacting ions to form adduct or product ions; (xxiv) an ion-atom reaction device for reacting ions to form adduct or product ions; (xxv) an ion-metastable ion reaction device for reacting ions to form adduct or product ions; (xxvi) an ion-metastable molecule reaction device for reacting ions to form adduct or product ions; and (xxvii) an ion-metastable atom reaction device for reacting ions to form adduct or product ions.

The mass spectrometer preferably further comprises acceleration means arranged and adapted to accelerate ions into the collision, fragmentation or reaction device wherein in a mode of operation at least 5%, 10%, 15%, 20%, 25%, 30%, 35%, 40%, 45%, 50%, 55%, 60%, 65%, 70%, 75%, 80%, 85%, 90%, 95% or 100% of the ions are caused to fragment or react upon entering the collision, fragmentation or reaction device.

The mass spectrometer preferably further comprises a control system arranged and adapted to switch or repeatedly switch the potential difference through which ions pass prior to entering the collision, fragmentation or reaction device between a relatively high fragmentation or reaction mode of operation wherein ions are substantially fragmented or reacted upon entering the collision, fragmentation or reaction device and a relatively low fragmentation or reaction mode of operation wherein substantially fewer ions are fragmented or reacted or wherein substantially no ions are fragmented or reacted upon entering the collision, fragmentation or reaction device.

In the relatively high fragmentation or reaction mode of operation ions entering the collision, fragmentation or reaction device are preferably accelerated through a potential difference selected from the group consisting of: (i) $\geq$10 V; (ii) $\geq$20 V; (iii) $\geq$30 V; (iv) $\geq$40 V; (v) $\geq$50 V; (vi) $\geq$60 V; (vii) $\geq$70 V; (viii) $\geq$80 V; (ix) $\geq$90 V; (x) $\geq$100 V; (xi) $\geq$110 V; (xii) $\geq$120 V; (xiii) $\geq$130 V; (xiv) $\geq$140 V; (xv) $\geq$150 V; (xvi) $\geq$160 V; (xvii) $\geq$170 V; (xviii) $\geq$180 V; (xix) $\geq$190 V; and (xx) $\geq$200 V.

In the relatively low fragmentation or reaction mode of operation ions entering the collision, fragmentation or reaction device are preferably accelerated through a potential difference selected from the group consisting of: (i) $\leq$20 V; (ii) $\leq$15 V; (iii) $\leq$10 V; (iv) $\leq$5V; and (v) $\leq$1V.

The control system is preferably arranged and adapted to switch the collision, fragmentation or reaction device between the relatively high fragmentation or reaction mode of operation and the relatively low fragmentation or reaction mode of operation at least once every 1 ms, 5 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, 100 ms, 200 ms, 300 ms, 400 ms, 500 ms, 600 ms, 700 ms, 800 ms, 900 ms, 1 s, 2 s, 3 s, 4 s, 5 s, 6 s, 7 s, 8 s, 9 s or 10 s.

The potential difference through which ions pass prior to entering the collision, fragmentation or reaction device may be varied, increased or decreased in use. The potential difference may be ramped, stepped, scanned or varied linearly or non-linearly with time in a substantially synchronised manner with the emergence of ions from the device. According to an embodiment the potential difference through which ions pass prior to entering the collision, fragmentation or reaction device may be varied, increased or decreased in use or the potential difference may be ramped, stepped, scanned or varied linearly or non-linearly with time in a substantially synchronised manner with the emergence of ions from the device and as a function of or in relation to either the mass to charge ratio of the ions which are predicted to emerge from the device as a function of time and/or the ion mobility of the ions which are predicted to emerge from the device as a function of time.

The collision, fragmentation or reaction device is preferably arranged and adapted to receive a beam of ions and to convert or partition the beam of ions such that at least 1, 2, 3, 4, 5, 6, 7, 8, 9, 10, 11, 12, 13, 14, 15, 16, 17, 18, 19 or 20 separate groups or packets of ions are confined and/or isolated in the collision, fragmentation or reaction device at any particular time, and wherein each group or packet of ions is separately confined and/or isolated in a separate axial potential well formed in the collision, fragmentation or reaction device.

In a mode of operation the device may be arranged and adapted to operate as a collision, fragmentation or reaction device.

In a mode of operation the device may be arranged and adapted to collisionally cool or thermalise ions within the device.

The mass spectrometer preferably further comprises an ion source. The ion source is preferably selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) a Thermospray ion source; (xviii) a Particle Beam ("PB") ion source; and (xix) a Flow Fast Atom Bombardment ("Flow FAB") ion source.

The mass spectrometer preferably further comprises a continuous or pulsed ion source.

According to the preferred embodiment singly charged ions having a first mass to charge ratio have a first transit or drift time t1 through the device in the first mode of operation and wherein singly charged ions having the first mass to charge ration have a second transit or drift time t2 through the device in the second mode of operation, wherein t2>t1. According to an embodiment the ratio t2/t1 may be in the range 1-2, 2-3, 3-4, 4-5, 5-6, 6-7, 8-9, 9-10, 10-11, 11-12, 12-13, 13-14, 14-15, 15-16, 16-17, 17-18, 18-19, 19-20, 20-25, 25-30, 30-35, 35-40, 40-45, 45-50, 50-60, 60-70, 70-80, 80-90, 90-100 or >100.

According to another aspect of the present invention there is provided a method of mass spectrometry comprising:
providing a device;
operating the device in a first mode of operation wherein ions are separated temporally within the device according to their ion mobility; and
operating the device in a second mode of operation wherein ions are separated temporally within the device according to their mass to charge ratio.

According to another aspect of the present invention there is provided a mass analyser comprising:
a plurality of electrodes; and
a device arranged and adapted to pulse an axial electric field ON and OFF within the mass analyser so that ions are axially accelerated without reaching a terminal velocity.

The mass analyser is preferably arranged to be maintained at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

According to another aspect of the present invention there is provided a method of mass analysing ions comprising:
providing a mass analyser comprising a plurality of electrodes; and
pulsing an axial electric field ON and OFF within the mass analyser so that ions are axially accelerated without reaching a terminal velocity.

The method preferably further comprises maintaining the mass analyser at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

According to another aspect of the present invention there is provided a mass analyser comprising:
a plurality of electrodes; and
a device arranged and adapted to repeatedly apply an axial electric field in a first direction and then to apply an axial electric field in a second direction which is opposed to the first direction so that ions are axially accelerated without reaching a terminal velocity.

The mass analyser is preferably arranged to be maintained at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

According to another aspect of the present invention there is provided a method of mass analysing ions comprising:
providing a mass analyser comprising a plurality of electrodes; and
repeatedly applying an axial electric field in a first direction and then applying an axial electric field in a second direction which is opposed to the first direction so that ions are axially accelerated without reaching a terminal velocity.

The method preferably further comprises maintaining the mass analyser at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

The preferred embodiment relates to a device wherein an applied axial electric field or fields may be switched between two modes of operation whilst the device is maintained at substantially the same operating pressure. In a first mode of operation the device is preferably arranged to separate ions predominantly according to their ion mobility. In a second mode of operation the device is preferably arranged to separate ions predominantly according to their mass to charge ratio. The preferred device therefore relates to a dual mode ion mobility-mass analyser device.

The preferred embodiment relates to a method of operating an ion mobility spectrometer or IMS device wherein in a mode of operation ions are prevented from reaching a steady state velocity as would be the case with a conventional ion mobility spectrometer or separator. In this mode of operation the separation of the ions is strongly dependent upon the mass to charge ratio of the ions rather than ion mobility. The ions are preferably repeatedly subjected to an electrical field for a relatively short period of time in the presence of a buffer gas. The ions may, for example, be subjected to an electrical field for a relatively short period of time by applying a time varying electrical field or alternatively by applying a combination of position and time varying electric fields.

With reference to a conventional drift tube ion mobility spectrometer, the general solution in terms of velocity for the equation of motion as given by Eqn. 1 is:

$$\frac{d}{dt}x = E\frac{q}{\lambda}\left(1 - e^{\frac{-\lambda t}{m}}\right) + Uoe^{\frac{-\lambda t}{m}} \quad (3)$$

wherein Uo is the velocity of the ion at time t=0.

The general solution of the equation of motion in terms of position is:

$$x = Xo + E\frac{q}{\lambda}t + E\frac{qm}{\lambda^2}\left(e^{\frac{-\lambda t}{m}} - 1\right) + Uo\frac{m}{\lambda}\left(1 - e^{\frac{-\lambda t}{m}}\right) \quad (4)$$

wherein Xo is the position of the ion at time t=0.

If Xo and Uo are set equal to zero and by defining $K=q/\lambda$ and $\tau=mK/q$, then the two equations become:

$$\frac{d}{dt}x = EK\left(1 - e^{\frac{-t}{\tau}}\right) \quad (5)$$

$$x = EKt - EK\tau\left(1 - e^{\frac{-t}{\tau}}\right) \quad (6)$$

Setting $t>>\tau$ we find that:

$$\frac{d}{dt}x = EK \quad (7)$$

$$x = EK(t - \tau) \quad (8)$$

The above general relationships hold for various ion mobility based separation techniques.

In the expressions given above, $\tau$ can be considered as the time constant associated with the time that an ion takes to reach an average steady state velocity. If the length of time t that the electric field is applied for is comparable with $\tau$ then the exponential term becomes significant and both the velocity and position become a function of mass to charge ratio and mobility.

Approximate expressions for velocity and position can be derived by expanding the exponential terms and are given below:

$$\frac{d}{dt}x = E\frac{q}{m}t\left(1 - \frac{t}{2!\tau} + \frac{t^2}{3!\tau^2} - \frac{t^3}{4!\tau^3} + \ldots\right) \quad (9)$$

$$x = E\frac{q}{2m}t^2\left(1 - \frac{t}{3\tau} + \frac{t^2}{12\tau^2} - \frac{t^3}{60\tau^3} + \ldots\right) \quad (10)$$

From the expressions given above it is apparent that for $t<\tau$, the velocity and position become strongly dependent upon mass to charge ratio. If the ions cease to experience the electric field after a time t, where $t<\tau$, then the velocity and position of an ion remain predominantly dependent upon the mass to charge ratio of the ion.

Similar expressions can be derived for the velocity and position of an ion as it slows down after an applied electric field has been switched OFF. Substituting E=0 gives the following equation for velocity:

$$\frac{d}{dt}x = Ue^{\frac{-t}{\tau}} \quad (11)$$

wherein U is the forward velocity of the ion at the time that the electric field is removed or switched OFF.

If ions lose substantially all or most of their forward velocity through collisions with gas molecules before they are subjected again to an electric field, then the average ion velocity will remain predominantly dependent upon the mass to charge ratio of the ion. For example, pulsing ON and OFF an electric field which is applied along the length of a linear ion mobility spectrometer or separator for relatively short periods of time (wherein the pulse duration is of the same order or less than the time constant $\tau$) will result in ion transit times which are predominantly mass to charge ratio dependent. A population of ions may be introduced substantially simultaneously into the ion mobility spectrometer or separator via an entrance end. The ions will then preferably emerge from an exit end of the ion mobility spectrometer or separator in order of their mass to charge ratio.

Embodiments of the present invention are contemplated wherein mass to charge ratio dependent separation of ions may be achieved in various ways including applying discrete time varying electric fields or by continuously applying a time varying electric field such as a sinusoidal electric field or an electric field having a curved, stepped or sinusoidal profile. Further embodiments are contemplated wherein combinations of these two approaches may be adopted such as ramping an applied electric field for a relatively short period of time.

According to another embodiment a static or DC axially inhomogeneous electric field may be applied in order to separate ions at least partially according to their mass to charge ratio. According to another embodiment a combination of a time varying axial electric field and an axially inhomogeneous electric field may be applied. Ions in an inhomogeneous electric field will move quickly from a region of relatively high electric field strength to a region of relatively low electric field strength. This will yield a similar effect to applying an electric field for a relatively short period of time and then removing the electric field.

According to an embodiment a travelling wave ion mobility spectrometer or separator may be provided. The ion mobility spectrometer or separator preferably comprises a series of electrodes having apertures through which ions are preferably transmitted in use. A travelling wave is preferably generated by applying one or more transient DC voltages or potentials or one or more transient DC voltage or potential waveforms to one or more of the electrodes. After a short time interval the transient DC voltage or potential which is preferably applied to one or more electrodes is preferably shifted to a neighbouring electrode or electrodes in the direction in which the ions are directed to travel. If the velocity of the travelling wave is increased then ions will experience the field due to the transient DC voltage or potential at a higher frequency but for a shorter period of time. Therefore, under appropriate conditions, as the wave velocity is increased the separation of ions may become more mass to charge ratio dependent as opposed to ion mobility dependent.

Advantageously, the preferred device or ion mobility-mass analyser according to a preferred embodiment of the present invention is capable of functioning as a mass analyser at a relatively high pressure in the range of $10^{-2}$ mbar to 10 mbar. This operating pressure is substantially higher than the operating pressure of commercial mass analysers wherein the pressure needs to be maintained at a low pressure so that the mean free path of gas molecules is substantially longer than the flight path of ions within the mass analyser. The relatively high operating pressure of an ion mobility-mass analyser according to an embodiment of the present invention is comparable with the pressure within an ion guide which may be provided which guides ions from an ion source to other ion-optical components of a mass spectrometer. The relatively high operating pressure of the preferred device is also comparable with the operating pressure of a gas collision cell or ion mobility spectrometer or separator. In order to maintain the preferred device at a relatively high pressure it is only necessary to use a roughing pump such as a rotary pump or scroll pump. Therefore, advantageously, it is not necessary to provide a more complex and expensive fine vacuum pump such as a turbomolecular pump or diffusion pump in order to maintain the preferred ion mobility-mass analyser device at a relatively low pressure.

The preferred device when operated in a mass to charge ratio separation mode of operation may have a relatively low mass resolution. For example, the mass resolution may be in the range of 10 to 20 (FWHM). However, the preferred device has a high transmission efficiency since there are no appreciable losses. Ions are preferably radially confined within the preferred device and substantially all ions are preferably onwardly transmitted in order of their mass to charge ratio. An ion trap or ion storage region or device may be provided upstream of the preferred device and ions may be accumulated and stored in the ion trap or ion storage region whilst other ions are being separated according to their mass to charge ratio within the preferred device. The preferred device preferably comprises a travelling wave RF ion guide. The combination of an upstream ion trap or ion storage region or device and an ion mobility-mass analyser according to an embodiment of the present invention enables a high duty cycle to be achieved.

According to an embodiment a preferred ion mobility-mass analyser may be provided in combination with an upstream ion trap or ion storage region or device and a downstream second mass analyser. The combination of an upstream ion trap or ion storage region or device, an ion mobility-mass analyser according to an embodiment of the present invention and a high resolution mass analyser arranged downstream of the preferred ion mobility-mass analyser preferably enables a high duty cycle, high transmission and high mass resolution mass spectrometer to be provided.

An ion mobility-mass analyser according to an embodiment of the present invention may be provided in conjunction with or in combination with another type of mass analyser. For example, a preferred ion mobility-mass analyser may be provided in combination with an axial acceleration Time of Flight mass analyser, an orthogonal acceleration Time of Flight mass analyser, a 3D quadrupole ion trap, a linear quadrupole ion trap, a quadrupole mass filter, a magnetic sector mass analyser, an Ion Cyclotron Resonance mass analyser or an orbitrap mass analyser. Variations of the aforementioned types of mass analyser which employ Fourier Transforms of mass dependent resonance frequencies may also be provided in combination with an ion mobility-mass analyser according to an embodiment of the present invention.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
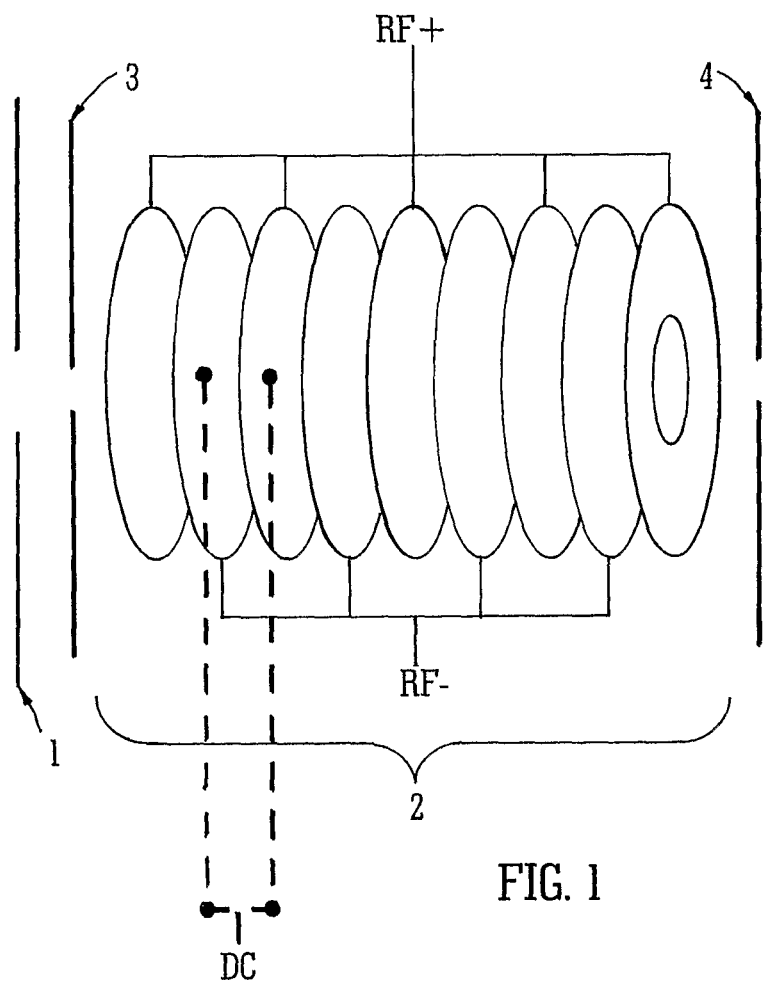
FIG. 1 shows an ion mobility-mass analyser according to an embodiment of the present invention.

An ion mobility-mass analyser according to a preferred embodiment of the present invention will now be described with reference to FIG. 1. The preferred device preferably comprises a gate electrode 1, an entrance electrode 3, a ring stack RF ion guide 2 and an exit electrode 4. The ion guide 2 preferably comprises a plurality of electrodes having apertures through which ions are preferably transmitted in use. Opposite phases of an AC or RF voltage are preferably applied to adjacent electrodes in order to generate radial pseudo-potential well which preferably acts to confine ions radially within the ion guide 2. As ions enter the ion guide 2 ions preferably experience an RF field that serves to confine ions radially within the ion guide 2. This enables the transmission of ions through the ion guide 2 to be maximised at intermediate pressures.

According to another embodiment a single electrode may be provided instead of a separate gate electrode 1 and entrance electrode 3. Ions are preferably periodically pulsed into the RF ion guide 2 by pulsing the gate electrode 1 or another electrode which may be arranged upstream of the ion guide 2.

According to a preferred embodiment an additional or transient DC voltage or potential or one or more transient DC voltage or potential waveforms may be applied to one or more of the ring electrodes 2. According to an embodiment as shown in FIG. 1, an additional or transient DC potential may be applied simultaneously to two electrodes. The transient DC voltage or potential is preferably applied to one or more electrodes for a relatively short period of time. The DC voltage or potential is then preferably switched to or applied to an adjacent pair of electrodes. A travelling wave or transient DC voltage or potential is therefore preferably applied to the electrodes according to an embodiment. The velocity and amplitude of, the travelling wave is preferably programmable and the velocity and/or amplitude of the travelling wave may be varied with time. According to the preferred embodiment one or more transient DC voltages or potentials or one or more transient DC voltage or potential waveforms may be applied to the electrodes in order to urge at least some ions along the length of the ion mobility-mass analyser.

According to the preferred embodiment the ion guide 2 when operated in a first or ion mobility separation mode of operation may be maintained at a pressure in the range $10^{-2}$ to 100 mbar, or more preferably in the range $10^{-1}$ to 10 mbar. According to the preferred embodiment the ion guide 2 may also be operated in a second or mass to charge ratio separation mode of operation. When the ion guide 2 is operated in a second or mass to charge ratio separation mode of operation the ion guide 2 may also be maintained at substantially the same pressure i.e. in the range $10^{-2}$ to 100 mbar, or more preferably in the range $10^{-1}$ to 10 mbar.

Figure 2:
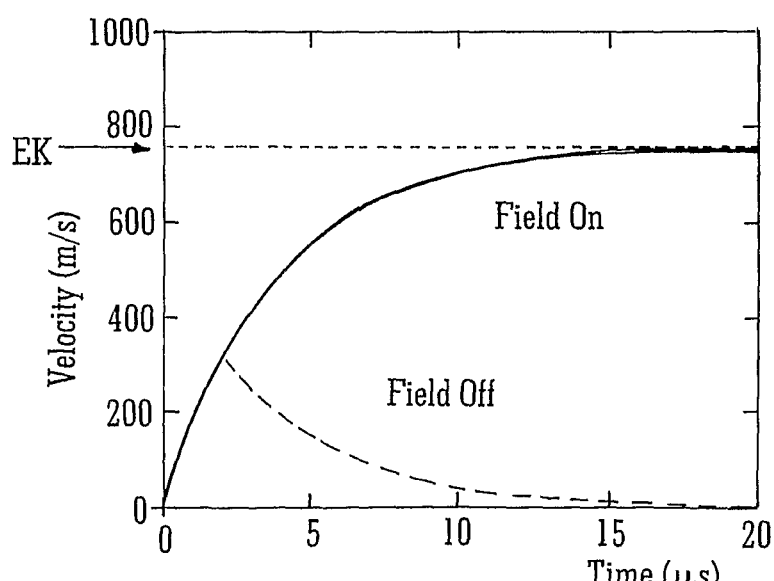
FIG. 2 shows a graph of the velocity of an ion as a function of time when a preferred ion mobility-mass analyser is operated in an ion mobility separation mode of operation wherein an axial electric field is applied continuously and the velocity of an ion as a function of time when a preferred ion mobility-mass analyser is operated in a mass to charge ratio separation mode of operation wherein an axial electric field is applied in short pulses.

FIG. 2 shows a plot (indicated by the solid line) of the velocity of an ion as a function of time when the preferred device is operated in a first or ion mobility mode of operation. When the preferred device is operated in the first or ion mobility mode of operation the device operates, in effect, as an ion mobility spectrometer or separator so that ions are separated temporally according to their ion mobility. In this mode of operation an axial electric field is preferably applied or maintained substantially continuously along the length of the device. FIG. 2 also shows a plot (indicated by a dashed line) of the velocity of an ion as a function of time when the preferred device is operated in a second or mass to charge ratio separation mode of operation. When the preferred device is operated in the second or mass to charge ratio separation mode of operation the device operates, in effect, as a mass to charge ratio separator or mass analyser so that ions are separated temporally according to their mass to charge ratio. In this mode of operation an axial electric field is preferably applied in relatively short pulses or for a relatively short period of time along the length of the device.

The data shown in FIG. 2 corresponds to an ion having a mass to charge ratio of 950 and an ion mobility of 0.39 $m^2/V/s$. The solid line shows the velocity of the ion as it accelerates from an initial zero velocity up to a steady state velocity of approximately E×K, wherein E is the electric field and K is the ion mobility. In this mode of operation a voltage is preferably applied substantially continuously to the electrodes and the velocity of the ion is preferably determined predominantly by the mobility of the ion.

The dashed line shown in FIG. 2 shows the velocity of the ion when the preferred device is operated in a second or mass to charge ratio separation mode of operation wherein the applied axial electric field is switched OFF after 2 μs. In the second mode of operation the ion has not had sufficient time to and is substantially prevented from reaching a steady state velocity. If the forward velocity of the ion is allowed to decay to a relatively low value before a subsequent pulse or axial electric field is applied, then the average velocity of the ion will be strongly dependent upon the mass to charge ratio of the ion.

According to an embodiment a preferred device may be switched between an operating mode wherein a substantially continuous axial electric field is maintained and another operating mode wherein an appropriate repetitive short lived transient axial electric field is preferably maintained or applied whilst operating the preferred device at an appropriate gas pressure. The preferred device may therefore be switched between two modes of operation wherein ions are separated temporally according to their ion mobility in a first mode of operation and are separated temporally according to their mass to charge ratio in a second mode of operation.

Figure 3:
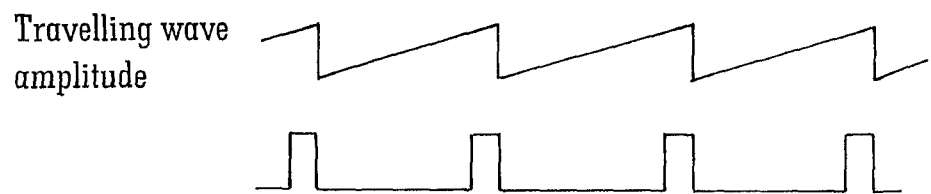
FIG. 3 shows an embodiment wherein a preferred ion mobility-mass analyser is coupled to an orthogonal acceleration Time of Flight analyser via a transfer lens.
Figure 3:
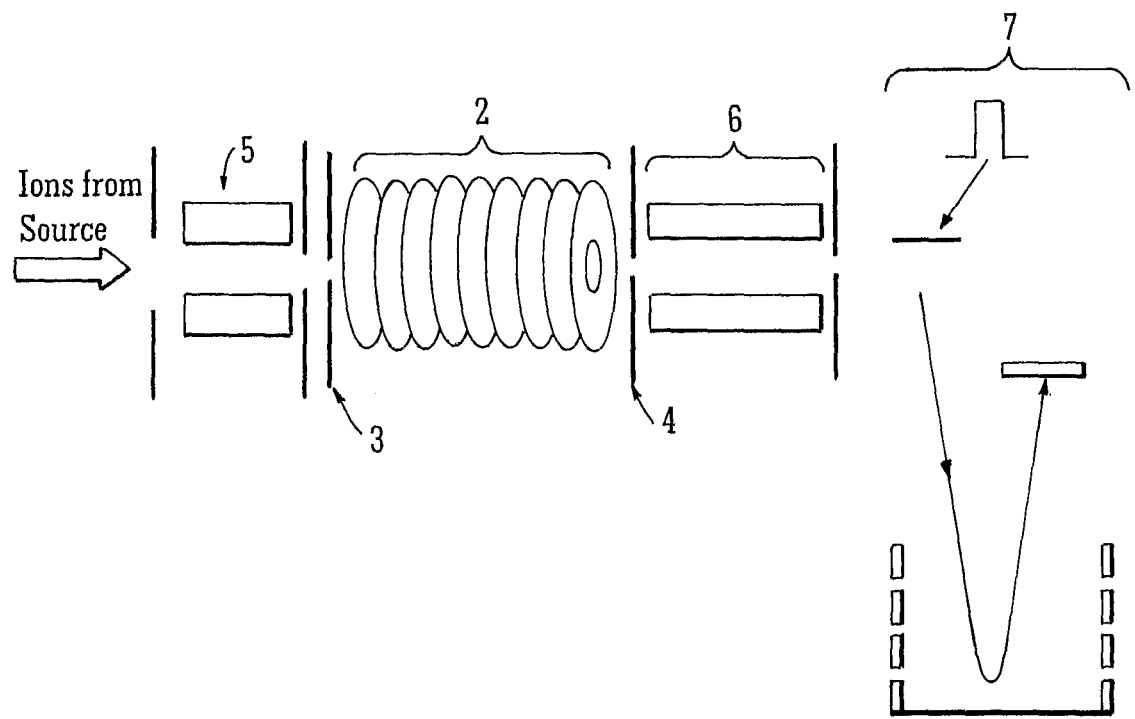

FIG. 3 shows an embodiment of the present invention wherein an ion mobility-mass analyser 2 according to an embodiment of the present invention is coupled to an orthogonal acceleration Time of Flight mass analyser 7 via a transfer lens 6. Ions are preferably generated by an ion source and are then preferably accumulated in an ion trap 5 which is preferably arranged upstream of the ion mobility-mass analyser 2. Ions are preferably periodically released from the ion trap 5 by pulsing a gate electrode which is preferably arranged at the exit of the ion trap 5 and which is also preferably upstream of the ion mobility-mass analyser 2. At the instance when a pulse of ions is released from the ion trap 5, a travelling wave voltage or one or more transient DC voltages or potentials are preferably applied to the electrodes of the ion mobility-mass analyser 2. The amplitude of the travelling wave voltage is preferably arranged initially to have a minimum or relatively low voltage or amplitude. According to an embodiment the amplitude of the travelling wave voltage may, for example, initially be set to zero. According to an embodiment the amplitude of the travelling wave voltage is then preferably ramped in a linear or other manner to a final maximum voltage.

Ions preferably pass through the ion mobility-mass analyser 2 and preferably emerge from the exit of the ion mobility-mass analyser 2. As ions exit the RF ion guide 2 or ion mobility-mass analyser the ions preferably pass through a transfer lens 6. The ions are then preferably onwardly transmitted to an orthogonal acceleration Time of Flight mass analyser 7. At least some of the ions which enter the Time of Flight mass analyser 7 are then preferably mass analysed by the orthogonal acceleration Time of Flight mass analyser 7 by applying a orthogonal acceleration voltage to an orthogonal acceleration electrode.

In order to demonstrate the various different modes of operation, two experiments were performed wherein a protein digest was infused into a mass spectrometer which was arranged substantially as shown in FIG. 3. The ion mobility-mass analyser 2 was initially operated in a first mode of operation wherein ions were arranged to be separated temporally according to their ion mobility. The pressure in the ion guide 2 was set to 1 mbar Helium. A gate pulse was applied to an electrode 3 at the exit of the ion trap 5 which was 200 μs wide and which had a period of 13 ms. The travelling wave amplitude (i.e. the amplitude of the one or more transient DC voltages or potentials which were applied to the electrodes of the preferred device 2) was ramped linearly from 3 V to 7 V over the time period between subsequent gate pulses. The wave pattern was shifted every 10 μs resulting in a travelling wave being applied to the ion guide 2 which had an average velocity of 300 m/s.

Figure 4:
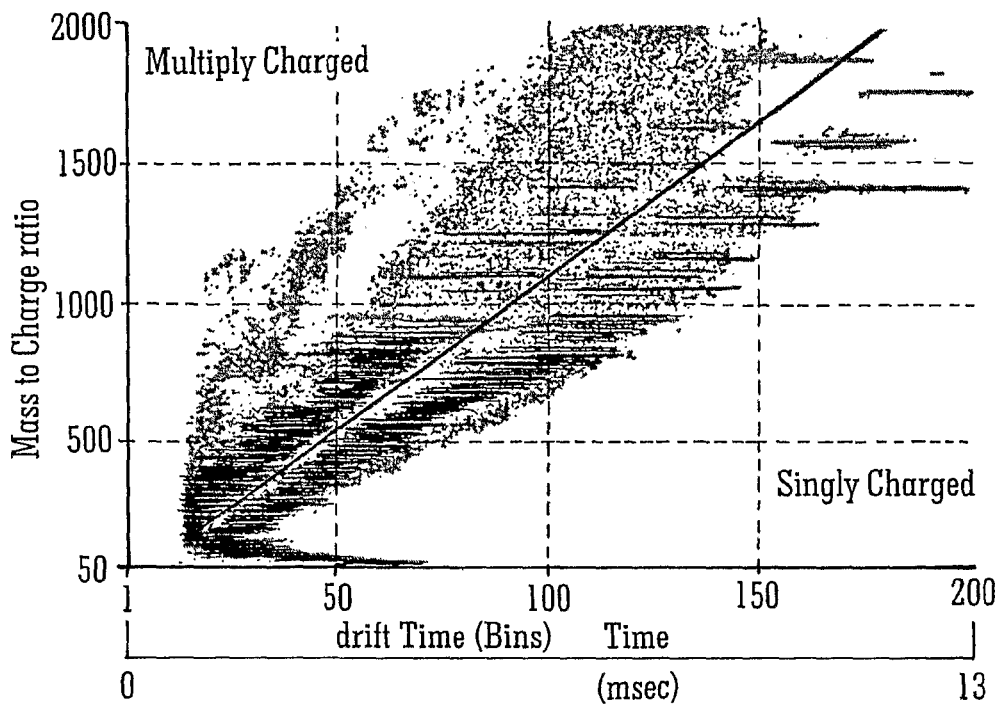
FIG. 4 shows the output of an ion mobility-mass analyser according to an embodiment of the present invention when the ion mobility-mass analyser is operated in an ion mobility separation mode of operation.

FIG. 4 shows the results of the first experiment in the form of a 2D plot. The intensities are shown on a logarithmic inverse grey scale with black being the most intense. The data exhibits the classical features associated with the separation of ions according to their ion mobility. Charge state separation bands can be deduced and there is only an approximate mass to charge ratio correlation for ions having a given charge state.

A second experiment was performed by reducing the wave pattern shift time interval from 10 μs to 2 μs. As a result, the average velocity of the travelling wave was increased from 300 m/s to 1500 m/s. For reference, a doubly charged peptide ion having a mass to charge ratio of 950 in 1 mbar helium may be considered as having an ion mobility of approximately 0.39 $m^2V^{-1}s^{-1}$. This corresponds with a time constant of $\tau=km/q=\sim3.8$ μs. In the second experiment the travelling wave amplitude was ramped linearly from 8 to 20 V over the time period between subsequent pulses. The time period between subsequent pulses was increased to 80 ms.

Figure 5:
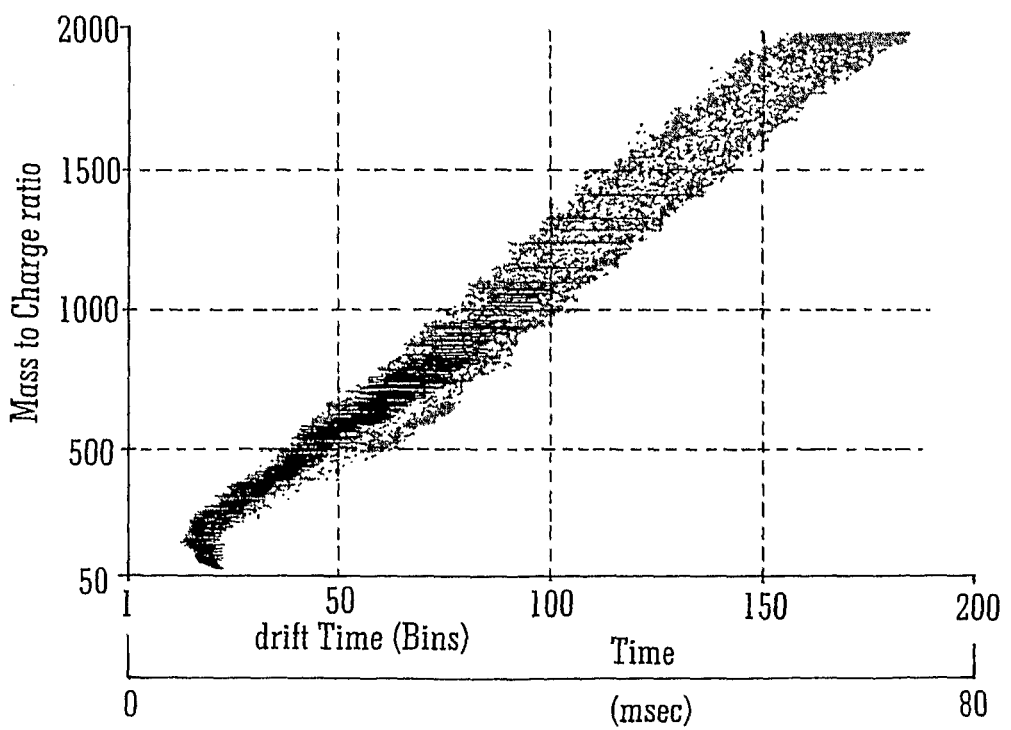
FIG. 5 shows the output of an ion mobility-mass analyser according to an embodiment of the present invention when the ion mobility-mass analyser is operated in a mass to charge ratio separation mode of operation.

FIG. 5 shows the results of the second experiment in the form of a 2D plot. The intensities are shown on a logarithmic inverse grey scale with black being the most intense. The data exhibits a strong mass to charge ratio dependence and has lost the charge-based separation which is observed when ions are separated according to their ion mobility.

Although the preferred ion mobility-mass analyser 2 is arranged to transmit onwardly substantially all ions in either mode of operation, the dual mode device 2 may not have as high a specificity as a conventional mass to charge ratio mass filter or mass analyser such as a quadrupole rod set mass filter or mass analyser when the dual mode device 2 is operated in a mass to charge ratio separation mode of operation. The effective resolution of the dual mode device 2 when operated in a mass to charge ratio separation mode may, for example, be in the range 10 to 20 whereas the resolution of a conventional quadrupole mass to charge ratio filter may be unit mass (i.e. a conventional quadrupole mass filter may have a resolution of 100 at mass to charge ratio 100, a resolution of 200 at mass to charge ratio 200, a resolution of 500 at mass to charge ratio 500 etc.).

Figure 6:
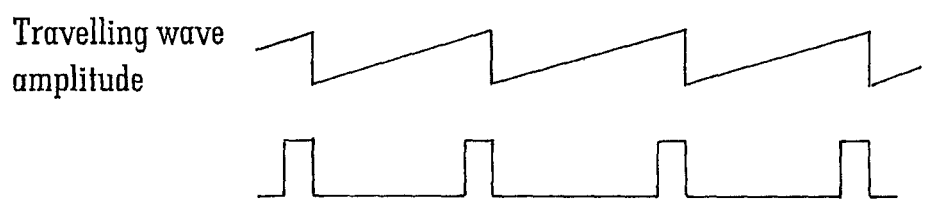
FIG. 6 shows an embodiment wherein a preferred ion mobility-mass analyser is coupled to scanning quadrupole rod set mass analyser.
Figure 6:
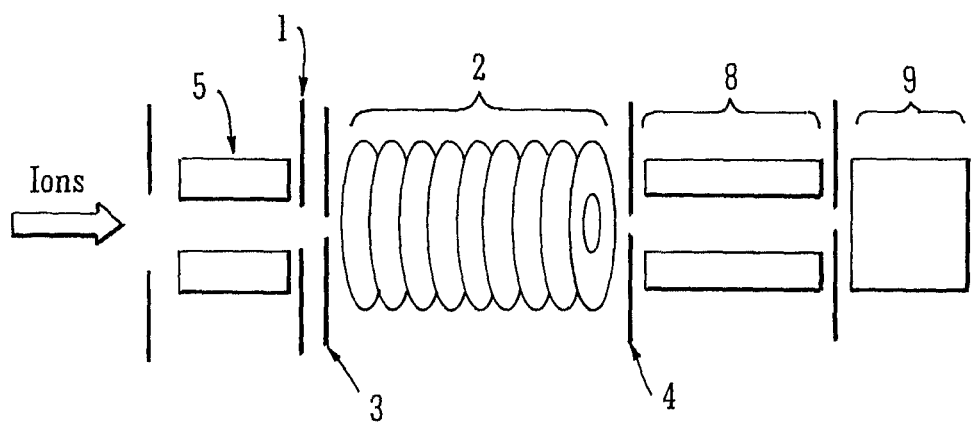

FIG. 6 shows an embodiment wherein a mass filter 8 is arranged downstream of an ion mobility-mass analyser 2 according to a preferred embodiment. An ion detector 9 is preferably arranged downstream of the mass filter 8. The mass filter 8 preferably comprises a quadrupole rod set mass filter 8 although other types of mass filter may be provided. The mass filter 8 may be arranged in a mode of operation to transmit substantially all ions. Alternatively, the mass filter 8 may be arranged to transmit only ions of interest having certain specific mass to charge ratios.

The preferred device 2 may be coupled to a high resolution scanning/stepping device such as a quadrupole rod set mass analyser in order to improve the overall instrument duty cycle and sensitivity. The mass to charge ratio of ions exiting the preferred device 2 will according to the preferred embodiment preferably increase approximately or substantially linearly with time. At any given time the mass to charge ratio range of ions exiting or emerging from the preferred device 2 will be relatively restricted. Therefore, all ions having a particular mass to charge ratio will preferably exit or emerge from the preferred device 2 during a relatively narrow or short time period. According to an embodiment of the present invention the mass to charge ratio transmission window of the scanning quadrupole rod set mass analyser 8 may be synchronised with the mass to charge ratio of ions which are predicted to exit or emerge from the preferred device 2. As a result, the duty cycle of the scanning quadrupole rod set mass analyser 8 can advantageously be increased.

A quadrupole rod set mass filter or mass analyser 8 will have a maximum scan rate which will be dependent upon the length of the quadrupole rod set. The maximum scan rate may, for example, be of the order of 100 ms when scanning across a mass range of 1000 daltons. According to an embodiment an ion mobility-mass analyser 2 according to an embodiment of the present invention may be used in conjunction with or in combination with a quadrupole rod set mass filter 8. According to this embodiment the preferred device 2 may be operated such that the cycle time of the preferred device 2 is increased from say 10 ms to be of the order of 100 ms. In the mass to charge ratio separation experiment, the results of which are shown in FIG. 5, it may be noted that the 80 ms scan time is generally compatible with the maximum scan rate of a typical quadrupole rod set mass filter.

According to another embodiment the mass to charge ratio transmission window of a quadrupole rod set mass analyser 8 arranged downstream of an ion mobility-mass analyser 2 according to an embodiment of the present invention may be stepped to a limited number of pre-determined mass to charge ratio values in order to synchronise with the mass to charge ratio of ions exiting or emerging from the preferred device 2. In this way the transmission efficiency and duty cycle of the quadrupole rod set mass filter or mass analyser 8 may be increased for a mode of operation wherein only ions having specific mass to charge ratios are of potential interest.

The mass filter or mass analyser 8 may be set to switch to a number of pre-selected or pre-determined mass to charge ratios at pre-selected or pre-determined times during the course of the cycle time of the preferred ion mobility-mass analyser 2. The pre-selected or pre-determined mass to charge ratios may be chosen, for example, to correspond with the mass to charge ratios of a series of specific fragment ions of interest. The pre-selected or pre-determined times may be arranged to encompass, for example, the exit times from the preferred ion mobility-mass analyser 2 of particular fragment ions of interest. More than one species of fragment ion may be measured with the specificity of a high resolution mass filter but advantageously without any loss in duty cycle and therefore without any loss in sensitivity.

According to an embodiment parent or precursor ions having one or more specific mass to charge ratios may be arranged to be transmitted through a first mass filter arranged upstream of the preferred ion mobility-mass analyser 2. Parent or precursor ions of interest may then be fragmented in a collision or fragmentation cell. The resulting fragment or daughter ions may then be passed to an ion mobility-mass analyser 2 according to an embodiment of the present invention. The fragment or daughter ions are then preferably separated temporally in the ion mobility-mass analyser 2. Fragment or daughter ions having one or more specific mass to charge ratios may then be transmitted onwardly by a second mass filter which is preferably arranged downstream of the preferred ion mobility-mass analyser 2. The fragment or daughter ions which are transmitted onwardly by the second mass filter are then preferably detected. The first mass filter and the second mass filter preferably comprise a quadrupole rod set mass filter. However, other embodiments are contemplated wherein the first mass filter and/or the second mass filter may comprise an alternative form of mass filter.

With reference to FIG. 6, a first quadrupole mass filter (not shown) may be provided upstream of the ion trap or ion trapping region 5 which is preferably operated as a collision cell and/or ion trap 5. An ion mobility-mass analyser 2 according to a preferred embodiment is preferably arranged downstream of the collision cell and/or ion trap 5. A second quadrupole mass filter 8 or mass analyser is preferably arranged downstream of the preferred ion mobility-mass analyser 2 and an ion detector 9 is preferably arranged downstream of the second quadrupole mass filter 8.

Parent or precursor ions which are onwardly transmitted by the first quadrupole mass filter are preferably received by and fragmented in the gas collision cell and/or ion trap 5. The collision cell and/or ion trap 5 is preferably maintained at a pressure between $10^{-4}$ mbar and 1 mbar, or more preferably between $10^{-3}$ and $10^{-1}$ mbar. The collision cell and/or ion trap 5 preferably comprises an RF ion guide wherein ions are preferably confined close to the central axis even when undergoing collisions with background gas molecules. The collision cell and/or ion trap 5 may comprise a multi-pole rod set ion guide wherein a RF voltage is preferably applied between neighbouring rods or electrodes. Alternatively, the collision cell and/or ion trap 5 may comprise a ring stack ion guide wherein an AC or RF voltage is preferably applied between neighbouring rings. Other embodiments are contemplated wherein the collision cell and/or ion trap 5 may comprise other forms of ion guide or ion trap. Ions are preferably arranged to enter the collision cell and/or ion trap 5 with an energy of at least 10 eV and preferably undergo multiple collisions with gas molecules and hence are induced to fragment by Collision Induced Disassociation.

The gas collision cell and/or ion trap 5 may additionally be used to store ions and release ions in pulses to the preferred ion mobility-mass analyser 2. A plate 1 or other electrode may be arranged at the exit of the gas collision cell and/or ion trap 5 and may be set or maintained at a voltage or potential such as to form a potential barrier thereby preventing ions from exiting the gas collision cell and/or ion trap 5. For positive ions, the plate 1 or other electrode may be maintained at a potential of about +10 V with respect to the other electrodes forming the gas collision cell and/or ion trap 5 in order to confine or retain ions axially within the gas collision cell and/or ion trap 5. A similar plate or electrode may be provided at a similar potential at the entrance to the gas collision cell and/or ion trap 5 in order to prevent ions from leaving or exiting the gas collision cell and/or ion trap 5 axially via the entrance.

The potential on the plate 1 or electrode arranged at the exit of the gas collision cell and/or ion trap 5 may according to an embodiment be lowered momentarily to 0 V, or less than 0 V with respect to the potential of the other electrodes forming the gas collision cell and/or ion trap 5. As a result, ions are preferably released in a pulse from the gas collision cell and/or ion trap 5 and are preferably directed towards and into the ion mobility-mass analyser 2. A travelling wave or one of more transient DC voltages or potentials or one or more transient DC voltage or potential waveforms are preferably applied to the electrodes of the ion mobility-mass analyser 2. The velocity of the travelling wave or one or more transient DC voltages or potentials or one or more transient DC voltage or potential waveforms applied to the electrodes of the preferred ion mobility-mass analyser 2 is preferably set so that ions are separated temporally according to their mass to charge ratio. The velocity of the travelling wave or one or more transient DC voltages or potentials or one or more transient DC voltage or potential waveforms is preferably also set in synchronism with the downstream quadrupole mass filter 8 which is preferably scanned or stepped in mass or mass to charge ratio.

Figure 7:
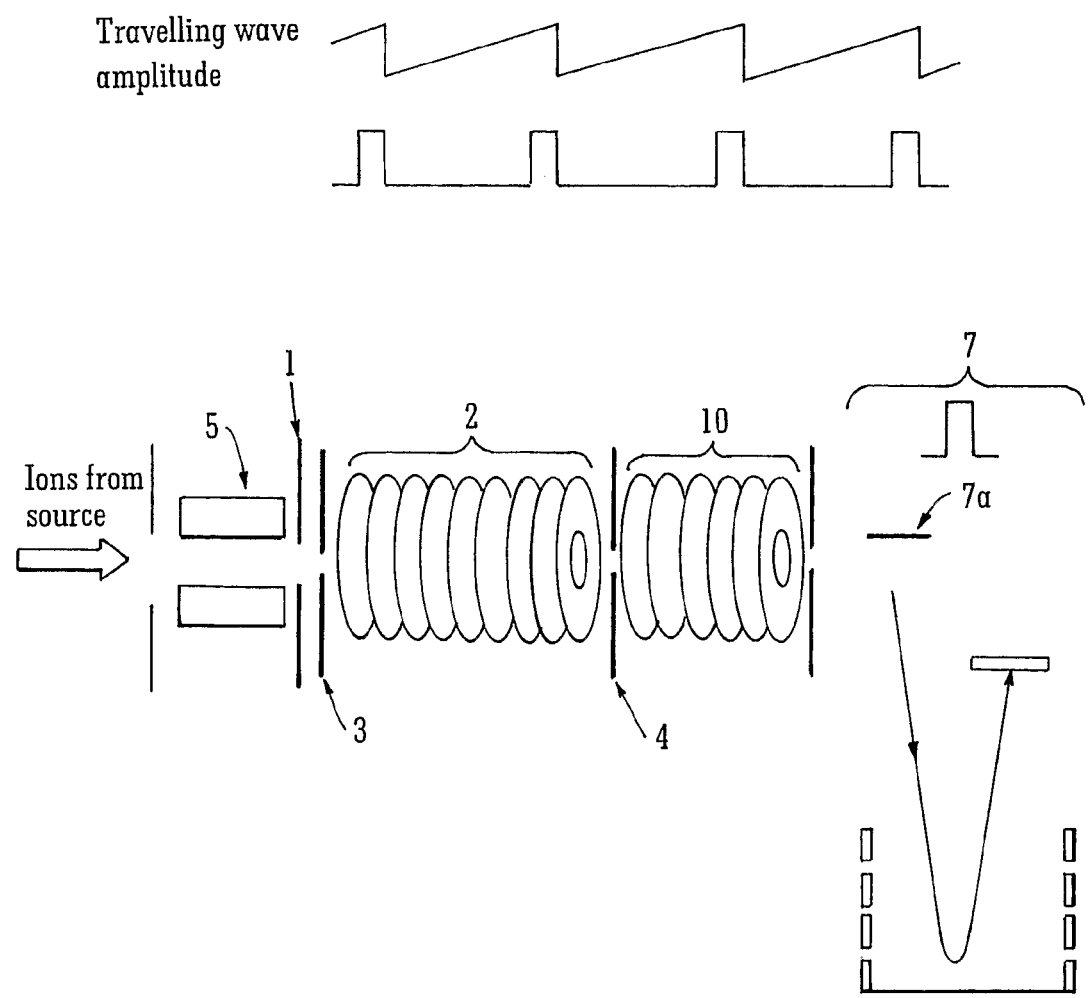
FIG. 7 shows an embodiment wherein an ion mobility-mass analyser is coupled to an orthogonal acceleration Time of Flight mass analyser via an ion guide.

FIG. 7 shows another embodiment of the present invention wherein a preferred ion mobility-mass analyser 2 is coupled to an orthogonal acceleration Time of Flight mass analyser 7 via an ion guide 10. The ion guide 10 preferably comprises a travelling wave ion guide 10. The ion mobility-mass analyser 2 and the ion guide 10 preferably enable the duty cycle and sensitivity of the Time of Flight mass analyser 7 to be improved. Ions are preferably output from the preferred device 2 in a mass to charge ratio dependent and time dependent manner. The travelling wave ion guide 10 is preferably arranged to sample the output of ions from the preferred device 2. Ions having a restricted or relatively narrow range of mass to charge ratios preferably emerge from the ion mobility-mass analyser 2 at any given instance. The ions which emerge from the ion mobility-mass analyser 2 at any given instance are preferably confined within one or more axial potential wells which are preferably created in the travelling wave ion guide 10. The one or more axial potential wells are preferably translated along the length of the travelling wave ion guide 10. Axial potential wells are preferably continuously created within the ion guide 10 and are preferably continually transported along the length of the ion guide 10. As an axial potential well reaches the exit of the ion guide 10 ions are preferably released from the ion guide 10 and are preferably directed towards an orthogonal acceleration region of the orthogonal acceleration Time of Flight mass analyser 7. An orthogonal acceleration Time of Flight extraction pulse is preferably periodically applied to an orthogonal acceleration electrode 7a. The timing of the extraction pulse is preferably synchronised with the release of ions from the travelling wave ion guide 10 in order to maximise the transmission of ions from a given axial potential well into the drift region of the orthogonal acceleration Time of Flight mass analyser 7.

According to this embodiment a sampling duty cycle of substantially 100% may be achieved. The preferred device 2 and the travelling wave ion guide 10 are preferably relatively closely coupled so that ions which emerge from or exit the preferred device 2 are preferably transported in a succession of packets or axial potential wells along the length of the ion guide 10. The ions are preferably maintained in the ion guide 10 in substantially the same order that the ions emerge from the preferred device 2.

The orthogonal acceleration Time of Flight mass analyser is preferably positioned downstream of the travelling wave RF ion guide 10. The travelling wave ion guide 10 and the orthogonal acceleration Time of Flight mass spectrometer 7 are preferably sufficiently closely coupled such that each packet of ions which is preferably released from the exit of the travelling wave ion guide 10 is preferably sampled by the orthogonal acceleration Time of Flight mass spectrometer with a sampling duty cycle of substantially 100%.

According to an embodiment the ion mobility-mass analyser 2 may be operated in a first mode of operation so as function as an ion mobility spectrometer or separator. The cycle time may be arranged to be, for example, of the order of 10 ms and ions which emerge from the exit of the ion mobility-mass analyser 2 are preferably collected in one of, for example, 200 packets or axial potential wells which are preferably formed in the travelling wave ion guide 10. Ions are preferably translated along the length of the ion guide 10 and each wave or axial potential well of the travelling wave ion guide 10 preferably has a cycle time of 50 µs.

When the preferred device 2 is selected or arranged to operate in a second mode of operation as a mass to charge ratio separator or mass analyser then the cycle time is preferably increased to be of the order of, for example, 100 ms. Ions emerging from the preferred device 2 are preferably collected in one of, for example, 200 packets or axial potential wells which are preferably formed in the travelling wave ion guide 10. Each wave or axial potential well which is preferably formed or created in the travelling wave ion guide 10 is preferably arranged to have a cycle time of 500 μs. Each wave or axial potential well which is translated along the length of travelling wave ion guide 10 is preferably arranged to correspond with a corresponding cycle of operation of the orthogonal acceleration Time of Flight mass analyser 7. According to an embodiment the delay time between the release of a packet of ions from the travelling wave ion guide 10 and the application of an orthogonal acceleration pusher voltage to the pusher electrode 7a of the Time of Flight mass analyser 7 may be arranged to increase progressively with each cycle according to the mass to charge ratio of the ions within each packet.

According to another embodiment parent or precursor ions having one or more specific mass to charge ratios may be onwardly transmitted by a first mass filter (not shown). The ions are then preferably fragmented in a collision cell and/or ion trap 5. The resulting fragment or daughter ions are then preferably passed to the preferred device or ion mobility-mass analyser 2. The fragment or daughter ions are preferably separated temporally in the ion mobility-mass analyser 2. Fragment or daughter ions having one or more specific mass to charge ratios are then preferably onwardly transmitted to the orthogonal acceleration Time of Flight mass analyser 7 via a travelling wave ion guide 10. The ions are then subsequently mass analysed and detected. The first mass filter preferably comprises a quadrupole mass filter although other types of mass filter are also contemplated.

The mass spectrometer according to an embodiment of the present invention preferably comprises an ion source which is preferably provided at an upstream end of the mass spectrometer. The ion source may comprise a pulsed ion source such as a Laser Desorption Ionisation ("LDI") ion source, a Matrix Assisted Laser Desorption/Ionisation ("MALDI") ion source or an Desorption/Ionisation on Silicon ("DIOS") ion source. Alternatively, the mass spectrometer may comprise a continuous ion source. If the mass spectrometer comprises a continuous ion source then an ion trap 5 for storing ions and periodically releasing ions may preferably be provided downstream of the ion source. The continuous ion source may comprise an Electrospray Ionisation ("ESI") ion source, an Atmospheric Pressure Chemical Ionisation ("APCI") ion source, an Electron Impact ("EI") ion source, an Atmospheric Pressure Photon Ionisation ("APPI") ion source, a Chemical Ionisation ("CI") ion source, a Desorption Electrospray Ionisation ("DESI") ion source, an Atmospheric Pressure MALDI ("AP-MALDI") ion source, a Fast Atom Bombardment ("FAB") ion source, a Liquid Secondary Ion Mass Spectrometry ("LSIMS") ion source, a Field Ionisation ("FI") ion source or a Field Desorption ("FD") ion source. Other continuous or pseudo-continuous ion sources may also be used.

According to a less preferred embodiment the ion mobility-mass analyser 2 may comprise a plurality of electrodes having rectangular, square or elliptical apertures. Other less preferred embodiments are contemplated wherein the ion mobility-mass analyser 2 may comprise a segmented rod set ion guide.

According to the preferred embodiment ions are preferably pulsed into the preferred device 2 using a gate electrode. However, other embodiments are contemplated wherein a pulsed ion source such as a MALDI ion source may be used. According to this embodiment ions may be pulsed directly into the preferred device or ion mobility-mass analyser 2.

According to another embodiment, a fragmentation region or collision cell (not shown) may be provided after or downstream of the mass separation region or the preferred ion mobility-mass analyser 2. The potential difference between the ion mobility-mass analyser 2 and the fragmentation region may, according to one embodiment, be ramped up or otherwise varied as a function of the time between injection pulses so that ions which exit or emerge from the preferred ion mobility-mass analyser 2 at any given time are preferably fragmented in a substantially optimal manner.

Although the present invention has been described with reference to the preferred embodiments, it will be understood by those skilled in the art that various changes in form and detail may be made without departing from the scope of the invention as set forth in the accompanying claims.

The invention claimed is

1. A mass spectrometer comprising:
   an ion guide including a plurality of electrodes for separating ions temporally, and a means for applying an axial electric field substantially continuously along an axial length of the ion guide in a first mode of operation to separate ions temporally according to their ion mobility and for applying an axial electric field in a pulsed manner along the ion guide in a second mode of operation to separate ions according to their mass to charge ratio.

2. A mass spectrometer as claimed in claim 1, further comprising means arranged and adapted to confine ions radially within said ion guide.

3. A mass spectrometer as claimed in claim 1, wherein said means is arranged and adapted to apply the axial electric fields along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

4. A mass spectrometer as claimed in claim 1, wherein in said first mode of operation said the ion guide is arranged to be maintained at a pressure and in the second mode of operation the ion guide is also arranged to be maintained at the pressure.

5. A mass spectrometer as claimed in claim 3, wherein said means further comprises a DC voltage means for maintaining in said first mode of operation a non-zero DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

6. A mass spectrometer as claimed in claim 3, wherein said means further comprises transient DC voltage means arranged and adapted in said first mode of operation to apply one or more transient DC voltages or one or more transient DC voltage waveforms to at least some of the electrodes forming said ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

7. A mass spectrometer as claimed in claim 1, wherein in said first mode of operation ions are accelerated within said ion guide so that the ions substantially achieve a terminal velocity.

8. A mass spectrometer as claimed in claim 1, wherein in said first mode of operation at least a portion of said ion guide is arranged to be maintained at a pressure selected from the group consisting of: (i) >0.001 mbar; (ii) >0.01 mbar; (iii) >0.1 mbar; (iv) >1 mbar; (v) >10 mbar; (vi) >100 mbar; (vii) >1000 mbar; (viii) 0.001-1000 mbar; (ix) 0.001-0.1 mbar; (x) 0.1-10 mbar; (xi) 10-1000 mbar; (xii) 0.001-0.005mbar; (xiii) 0.005-0.010 mbar; (xiv) 0.01-0.05 mbar; (xv) 0.05-0.10 mbar; (xvi) 0.1-0.5 mbar; (xvii) 0.5-1.0 mbar; (xviii) 1-5 mbar; (xix) 5-10 mbar; (xx) 10-50 mbar; (xxi) 50-100 mbar; (xxii) 100-500 mbar; (xxii) 500-1000 mbar; and (xxiv) >1000 mbar.

9. A mass spectrometer as claimed in claim 1, wherein said means further comprises a DC voltage means for maintaining in said second mode of operation a non-zero DC voltage gradient along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide in order to urge at least some ions along at least a portion or at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

10. A mass spectrometer as claimed in claim 1, wherein said means further comprises transient DC voltage means arranged and adapted in said second mode of operation to apply one or more transient DC voltages or one or more transient DC voltage waveforms to at least some of the electrodes forming said ion guide in order to urge at least some ions along at least 5%, 10%, 15%, 20%, 25%, 30%, 35%, 40%, 45%, 50%, 55%, 60%, 65%, 70%, 75%, 80%, 85%, 90%, 95% or 100% of the axial length of said ion guide.

11. A mass spectrometer as claimed in claim 1, wherein in said second mode of operation ions are accelerated within said ion guide but are substantially prevented from achieving a terminal velocity or wherein said ions do not achieve a terminal velocity.

12. A mass spectrometer as claimed in claim 1, wherein in said second mode of operation at least a portion of said ion guide is arranged to be maintained at a pressure selected from the group consisting of: (i) >0.001 mbar; (ii) >0.01 mbar; (iii) >0.1 mbar; (iv) >1 mbar; (v) >10 mbar; (vi) >100 mbar; (vii) >1000 mbar; (viii) 0.001-1000 mbar; (ix) 0.001-0.1 mbar; (x) 0.1-10 mbar; (xi) 10-1000 mbar; (xii) 0.001-0.005 mbar; (xiii) 0.005-0.010 mbar; (xiv) 0.01-0.05 mbar; (xv) 0.05-0.10 mbar; (xvi) 0.1-0.5 mbar; (xvii) 0.5-1.0 mbar; (xviii) 1-5 mbar; (xix) 5-10 mbar; (xx) 10-50 mbar; (xxi) 50-100 mbar; (xxii) 100-500 mbar; (xxiii) 500-1000 mbar; and (xiv) >1000 mbar.

13. A method of mass spectrometry comprising:
operating an ion guide in a first mode of operation by applying an axial electric field substantially continuously along an axial length of the ion guide wherein ions are separated temporally within said ion guide according to their ion mobility; and
operating said ion guide in a second mode of operation by applying an axial electric field in a pulsed manner along the ion guide wherein ions are separated temporally within said ion guide according to their mass to charge ratio.

14. A method of mass analysing ions comprising:
providing an ion guide including a plurality of electrodes; and
pulsing an axial electric field by applying a time varying electrical field or alternatively by applying a combination of position and time varying electric fields, in the presence of a buffer gas, so that the ions are axially accelerated without reaching a terminal velocity and separation of the ions is dependent upon the mass to charge ratio of the ions rather than ion mobility.

15. A method as claimed in claim 14, further comprising maintaining said mass analyser at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

16. A method of mass analysing ions comprising:
repeatedly applying an axial electric field to a plurality of electrodes in a mass analyser in a first direction, in the presence of buffer gas, and then applying an axial electric field to the plurality of electrodes in a second direction which is opposed to said first direction so that ions are axially accelerated without reaching a terminal velocity.

17. A method as claimed in claim 16, further comprising maintaining said mass analyser at a pressure selected from the group consisting of: (i) 0.001-0.005 mbar; (ii) 0.005-0.010 mbar; (iii) 0.01-0.05 mbar; (iv) 0.05-0.10 mbar; (v) 0.1-0.5 mbar; (vi) 0.5-1.0 mbar; (vii) 1-5 mbar; (viii) 5-10 mbar; (ix) 10-50 mbar; (x) 50-100 mbar; (xi) 100-500 mbar; (xii) 500-1000 mbar; and (xiii) >1000 mbar.

18. A method of mass spectrometry as claimed in claim 13, wherein operating the ion guide in the first mode of operation includes filling the ion guide with a buffer gas and applying the axial electric field to the ions in the ion guide to cause the ions to reach a terminal velocity and separate temporally according to their ion mobility and, wherein operating said ion guide in the second mode of operation includes applying the axial electric field in the pulsed manner such that the ions in the ion guide do not reach a terminal velocity and are separated temporally according to their mass to charge ratio.

19. A mass spectrometer as claimed in claim 1, wherein in said second mode of operation said means is arranged and adapted to apply said axial electric field in said pulsed manner so that ions are accelerated within said ion guide but are substantially prevented from achieving a terminal velocity or wherein said ions do not achieve a terminal velocity.

\* \* \* \* \*